United States Patent [19]

Alvarez

[11] 4,401,654

[45] Aug. 30, 1983

[54] ANTICOAGULANT METHODS WITH SULFUR DIOXIDE

[75] Inventor: Jose A. A. Alvarez, Mexico, Mexico

[73] Assignee: T & R Chemicals, Inc., Clint, Tex.

[21] Appl. No.: 281,951

[22] Filed: Jul. 9, 1981

Related U.S. Application Data

[63] Continuation of Ser. No. 164,304, Jun. 30, 1980, abandoned.

[51] Int. Cl.³ .............................................. A61K 33/04
[52] U.S. Cl. ..................................................... 424/162
[58] Field of Search ........................................ 424/162

[56] References Cited

U.S. PATENT DOCUMENTS

| | | |
|---|---|---|
| 2,182,965 | 12/1939 | Ioannu . |
| 2,367,302 | 1/1945 | Moore . |
| 2,451,312 | 10/1948 | Arengo-Jones . |
| 3,105,790 | 10/1963 | Bartholmew . |
| 3,836,639 | 9/1974 | Teler ................................. 424/101 |
| 3,906,109 | 9/1975 | Roehm ............................. 424/325 |
| 3,975,551 | 8/1976 | Shatila ............................. 426/637 |

OTHER PUBLICATIONS

Kikugawa, J., Pharm Sci., vol. 61, 1972, pp. 1904–1907.
Rost, "Comparative Invst. of the Pharmacol. Effects of Organically Bonded Sulfurous Acids and of Neutral Sodium Sulfite", In Arb. A. D. Kaiserlichen Gesundheitsamte, vol. 21, 1904, p. 312.
Chao, Thrombos. Haemostas (Stuttg), vol. 35, 1976, pp. 717–736.
Shulman, Chem. Abs., vol. 47, 1953, p. 9386.
Gunnison, Fd. Cosmet. Toxicol., vol. 19, 1981, pp. 667–682.
Elias, Abstract of Thromb. Diath Haemorrh, vol. 18 (3–4), 1967, pp. 499–509.
Torda, Abs. of Anaesth. Intens. Care, 1, 293, (1973).
Bourbon, Abs. of J. Eur. Toxicol., vol. 4, No. 3, pp. 205–207 (1971).
Chem. Abs., 9th Coll. Index, p. 37336CS, vol. 82, Ab. No. 107247f (1975).
FDA Publication No. PB-265 508 (1976) entitled: "Evaluation of the Health Aspects of Sulfiting Agents as Food Ingredients".
Shapiro, C.A. 88,87752k (1978).
Rost et al., C.A. 7, 1551 (1913).
Rost et al., Arb. Kais Gesundh. 43, 187–303.
Ouyang et al., C.A. 82, 107251f (1975).
Chao et al., 85:91232 (1976).
Csaba et al., C.A. 20, 4103 (1932).
Reiss et al., C.A. 42, 2355 g–h (1948).
Kikugawa et al., J. Pharm. Sci. (1972) 61(12), pp. 1904–1907.
Richards et al., 43, 1869 (1949).

*Primary Examiner*—Anna P. Fagelson
*Attorney, Agent, or Firm*—Cushman, Darby & Cushman

[57] ABSTRACT

Solutions of sulfur dioxide are found to demonstrate anticoagulant and antithrombotic activity when used in pharmaceutically effective amounts.

6 Claims, No Drawings

ANTICOAGULANT METHODS WITH SULFUR DIOXIDE

CROSS REFERENCE TO RELATED APPLICATIONS

This application is a continuation of my earlier application Ser. No. 164,304 filed June 30, 1980, now abandoned.

BACKGROUND OF THE INVENTION

Sodium bisulfite (usually shown by formula to be NaHSO₃) has heretofore been used for many commercial purposes, such as a preservative for prevention of the deterioration of liquids such as food stuffs and pharmaceutical solids, and has been used medically externally for parasitic skin diseases and internally as a gastrointestinal antiseptic.

Anticoagulants and antithrombotics are used in a variety of clinical conditions including, for examples, chronic phlebitis, post-operative states to prevent thrombosis of deep veins (thereby to avoid, for example, development of pulmonary emboli), strokes, heart attacks, arterial blood clotting (as demonstrated, for example, by platelet aggregation).

An anticoagulant agent is a substance which inhibits coagulation of the blood.

An antithrombotic agent is a substance which inhibits formation or development of a thrombus (or thrombosis). For present patent purposes, it will be understood tht the term "thrombus" or equivalent includes "embolus" unless otherwise specifically indicated. In general, an antithrombotic agent may display anticoagulant activity.

BRIEF SUMMARY OF THE INVENTION

There has now been discovered an inorganic system which, when added to mammalian blood or plasma, produces an anticoagulant effect. The system comprises a solution of sulfur dioxide in water.

This system may be mixed if desired with inorganic salts of sulfurous acid which themselves are known to display anticoagulant and antithrombotic activity. These inorganic salts are selected from the group consisting of alkali metals, alkaline earth metals and ammonium salts of sulfites and bisulfites (including metabisulfites) and mixtures thereof. Alkali metal bisulfites are presently preferred such additives, and sodium bisulfite is a presently most preferred such additive.

Also, this system may be mixed if desired with certain organic salts of sulfurous acid which themselves are known to display anticoagulant and antithrombotic activity. Thus, these salts are selected from the group consisting of certain basic organic nitrogen compound salts of sulfites and bisulfites (including metabisulfites) and mixtures thereof. Lower trialkylamine bisulfites are presently preferred active agents, and triethylamine bisulfite salt is a presently most preferred active agent.

Suitable basic nitrogen compounds include lower alkyl amines (including primary, secondary, and tertiary amines), lower alkanol amines (including primary, second and tertiary amines), heterocyclic nitrogen containing compounds containing from 4 through 12 carbon atoms per molecule and from 1 through 3 nitrogen atoms per molecule, guanidine, tetra (lower alkyl) ureas, lower alkyl quaternary amines, lower alkanol quarternary amines, cyclohexylamine, and mixtures thereof.

The term "lower" as used herein has reference to a radical containing less than 6 carbon atoms each.

Examples of suitable lower alkylamines include methyl amine, dimethyl amine, trimethyl amine, ethyl amine, diethyl amine, triethyl amine, propyl amine, isopropyl amine, tripentyl amine, and the like. Trimethyl amine salts tend to be undesirable because of a strong associated odor.

Examples of suitable lower alkanol amines including ethanol amine, diethanol amine, triethanol amine, methyl diethanol amine, dimethyl ethanol amine, 2-amino propanol, 2-amino-2-methyl-1-propanol, 2-amino-2-ethyl-1, 3-propanediol, and 2 amino-2 ethyl-1, 3-propanediol, and the like.

Examples of suitable such heterocyclic nitrogen compounds including pyridine, piperazine, morpholine, imidazole oxazole, N-methyl morpholine, aminohexamethyleneimine, 2-amino-4-methylpyridine, 3 amino-1H-1,2,4-triazole, 2-amino-4-picoline, aminopromazine, betaaminopyridine, aminopyrine, 2-amino-4-methylthiazole, and the like. Lower alkyl or lower hydroxy alkyl substituted heterocyclics can be used.

The antithrombotic system of this invention with or without the above additives is used in a variety of clinical conditions, including, for example, acute deep vein thrombosis and prethrombotic states, such as myocardial infarction, stroke, cancer, and cardiac valve replacement, for example, to prevent thrombosis of deep veins, thereby to avoid development of pulmonary emboli. Some improvement in existing thrombi may also be achieved through the use of these agents, such as by promoting the absorption of existing thrombi by the body; study continues on this effect.

The mechanisms by which the system functions is presently unknown; however, a lengthening of normal blood coagulation time appears to be associated with use thereof in the manner taught by the present invention.

In one aspect, the present invention is directed to compounds useful as oral antithrombotic agents in human medicine.

In another aspect, the present invention is directed to a method for control by, and/or preventing of, an embolus or a thrombus in man by oral ingestion of a pharmaceutically effective amount of sodium bisulfite and/or other compounds within the scope of active agents of this invention.

In another aspect, the present invention provides symptomatic and objective improvement in a cardiovascular disease condition, such as an abnormal coagulation or an intravascular thrombosis, in man. By the term "symptomatic improvement", as used herein, reference is had to an improvement in a patient's subjective symptoms as reported by the patient. By the term "objective improvement", as used herein, reference is had to a measurable and objective change in the patient's condition.

In another aspect, the present invention provides a technique for inhibiting blood coagulation factors VII, IX, X, XI and XII and moderately factor VIII. (including prothrombin time and partial thromboplastin time).

Other and further aspects, objects, purposes advantages, aims, utilities, features and the like will be apparent to those skilled in the art from a reading of the present specification.

DETAILED DESCRIPTION

More particularly, this invention concerns a process for treating the blood or plasma of a human or other mammal with a solution of sulfur dioxide as an anticoagulant and antithrombotic.

Sulfur dioxide, sulfite and/or bisulfite anions do not normally occur in human tissues or blood, so far as is now known.

In general, a thrombotic condition is detectable from patient conditions symptomatically perceivable by skilled medical practitioner and well known to the art of medicine. Recently, it has been reported that an onset may be detected by a test known as the $^{125}$I-fibrinogen test which is reported in Archives of Surgery, Vol. 104, Page 152, 1972.

The present invention does not contemplate feeding a normal patient a system of this invention at a dosage indicated herein.

By the term "thrombotic condition" as used herein, reference is had both to:

(a) an existing thrombus (including an embolus) and
(b) an incipient thrombus (including an incipient embolus).

An "incipient thrombus" or "incipient thrombotic condition", as such term is used herein, can exist in a patient as a result of various conditions, such as, for examples:

(A) an operation or surgical procedure of any sort, particularly one involving deep vein damage or alteration);

(B) an injury (such as a bruise resulting from a blow of any sort);

(C) a myocardial infarction; and the like, as those skilled in medicine will appreciate.

An "existing thrombus" or "existing thrombotic condition", as such term is used herein, can exist in a patient as a result of an existing thrombus (including an embolus at a given location in a patient), as those skilled in medicine will readily appreciate.

Preferably, to practice this invention, one can follow a series of steps. A first step is to determine that a mammal or a human suffers from a thrombotic condition. Then, one starts orally feeding such patient at least one system of the present invention at an antithrombotically effective dose rate. Presently, it is believed that effective does rates fall in the range from about 1 to 50 mg (milligram) per kg (kilogram) of patient body weight per day with dose rates of from about 20 to 50 mg/kg per day being more preferred. Preferably, at least two spaced doses per day are employed although more spaced doses at such rates can be employed if desired.

After oral feeding has started, the dose rate is adjusted to a value which is sufficient to maintain blood coagulation factors within desired selected ranges. It is presently preferred, and convenient, to measure blood prothrombin time (PT) and blood partial thromboplastin time (PTT) which is accomplishable by known methods. For example, a system of this invention lengthens both PT and PTT. A system increases each of PT and PTT; the dose rate rate of a system is directly proportional to resulting PT and PTT values. Experience has shown that lengthening PT and PTT values ameliorates (including controls and prevents) a thrombotic condition. Consequently, oral use of a system at a suitable dose for an individual patient ameliorates that patient's thrombotic condition. Determining blood coagulation time, or determining a single blood coagulation factor is sufficient for practicing the invention.

Preferably, in one mode, the PT and PTT values are determined before dosing with a system is started, as when time permits. Preferably, dose rate adjustment is accomplished after oral consumption of a system has commenced using PT and PTT values, and the adjustment is carried out using such values. More preferably PT and PTT is carried out periodically, such as every 3 to 7 days, on a patient undergoing treatment under the practice of this invention.

A system can be consumed in the form of a capsule, a tablet, or the like in a solution or dry form. A particularly presently preferred field of use is post operative patient treatment, as when deep veins may be involved in, or threatened by, a thrombotic condition.

In one preferred mode of using this invention, an aqueous solution of from about 1 to 7 percent by weight of sulfur dioxide in water is prepared. Then such solution is orally consumed by a human at the total (or accumulated) dose rate ranging from about 1 to 50 mg per each kg of body weight per day, more preferably in the form of at least two spaced doses per day, and still more preferably in the form of at least three spaced doses per day, such a dose being preferably taken around meal time. Solid encapsulated active agents may be orally consumed alternatively.

In one such mode of using this invention, one achieves symptomatic and objective improvement by inhibiting intravascular thrombosis (including embolism).

As originally utilized, this invention was preferably practiced using a dilute aqueous solution of sulfur dioxide. Such solutions still represent a practical way of practicing this invention.

The water used in such a solution is preferably purified (e.g. filtered, deionized, distilled, or the like). After preparation, such a solution is preferably stored in a closed container to reduce oxidation.

Such an aqueous solution can be directly used in accordance with the teachings of this invention, in which even such a solution can be dispensed dropwise, or such a solution can be encapsulated, or the like, and used as measured dosage units, as desired. For example, an aqueous solution containing 5 weight percent of sodium bisulfite can be directly consumed by a patient as drops (e.g. from about 5 to 9 drops per meal for each of the two or three meals eaten by such patient per day, depending upon an individual patient's body weight, or the like).

Symptomatic improvement in varicose veins and in hemorrhoids has been observed when using a system at a dose rate of from about 1 to 4 mg/kg of body weight per day.

In order to lengthen blood coagulation time in a human, sulfur dioxide in solution has been found to be effective when given at a presently more preferred dose rate ranging from about 10 to 50 mg/kg of body weight, per day, though it is believed that larger and/or smaller doses can be used without departing from the spirit and scope of the present discovery.

EMBODIMENTS

The present invention is further illustrated by reference to the following case histories. Those skilled in the art will appreciate that other and further embodiments are obvious and within the spirit and scope of this invention from the teachings of these present examples taken with the accompanying specification.

EXAMPLE A

A solution of sulfur dioxide in water is prepared by dissolving (bubbling a purified grade of sulfur dioxide) in distilled water at room temperature to form a 2 percent by weight aqueous solution. The resulting substance is then titrated with alkali using phenolphthalein to verify concentration.

EXAMPLE B

A solution of sulfur dioxide in ethanol is prepared by dissolving a purified grade of sulfur dioxide in 95 percent ethanol at room temperature to form a 2 percent by weight alcoholic solution.

EXAMPLE C

A solution of sodium bisulfite is prepared by dissolving pharmaceutical grade (U.S.P. Grade) powdered sodium bisulfite (sodium metabisulfite) in distilled water at room temperature to form a 1 percent by weight aqueous solution.

Thereafter, purified $SO_2$ gas is bubbled into such solution to give a concentration of $SO_2$ in such solution of 1 percent by weight.

EXAMPLE 1

Example A is a system which when added to human or rabbit plasma in vitro is found to significantly prolong PT and PTT in a dose-related fashion. The system appears to be particularly active in inhibiting coagulation factors VII, IX, X, XI and XII. It has a moderate inhibitory effect on factor VIII. Its effects on fibrinogen (factor I) and factor V are quite mild.

EXAMPLE 2

Example B is a system which when added to human or rabbit plasma in vitro is found to significantly prolong PT and PTT in a dose related fashion. The agent is active in inhibiting various cogulation factors, including VII, IX, X, XI, and XII.

References for PT, PTT and assays of all the coagulation factors can be found in a standard textbook, entitled "Human Blood Coagulation, Haemostasis and Thrombosis", edited by Rosemary Biggs, published by Blackwell Scientific Publications, Oxford, England (2nd edition), pages 670–705, 1976.

EXAMPLE 3

A group of ten rats (5 male and 5 female are each orally fed Example C by gavage at a dose rate equivalent to about 40 milligrams per kilogram of body weight. The procedure is repeated using a dose rate of 20 mg/kg. It is believed that such a feeding with Example C results in prolonged PT and PTT. The dose responses also show that the change is related proportionally to the dosage.

EXAMPLE 4

Sodium bisulfite is found to be actively absorbed from the gut using Example B. Feeding of rats and mice with Example B with associated blood tests suggests that such feeding results in prolonged PT and PTT.

EXAMPLE 5

The solution of Example A is tested for anticoagulant properties using human blood plasma by measuring PT and PTT values in seconds. For PT, the reagent used is Thromboplastin C from Dade Chemical and for PTT the reagent used is APTT from General Diagnostics. The results are summarized in the following Table I:

TABLE I

| NUMBER OF REPEATS FOR TEST | PT (seconds) | PTT (seconds) |
|---|---|---|
| 1 | 37.7 | 105.9 |
| 2 | 37.3 | 100.9 |
| 3 | 37.3 | 102.3 |
| 4 | 37.2 | 101.7 |
| 5 | 36.7 | — |

For PT, the mean is 37.3 seconds compared to the PT for the untreated control of 10.5 seconds.

For PTT, the mean is 102.7 seconds compared to the PTT for the untreated control of 27.5 seconds.

The data thus demonstrates that the solution of Example A demonstrates strong anticoagulant activity.

References for PT, PTT and essays of all the coagulation factors can be found in a standard textbook, entitled "Human Blood Coagulation, Haemostasis and Thrombosis", edited by Rosemary Biggs, published by Blackwell Scientific Publications, Oxford, England (2nd edition), pages 670–705, 1976.

Suitable solvents for $SO_2$ in the practice of this invention include water, ethanol, 2-propanol, 1-propanol, acetone, ethyl acetate, ethyl formate, propylene glycol, dipropylene glycol, ethyl propionate, and the like.

It is believed that a system of this invention when mixed with inorganic salts of sulfurous acid as defined above and/or with organic salts or sulfurous acids as defined above may form synergistic compositions as regards their anticoagulant and antithrombotic effectiveness.

I claim:

1. A process for inhibiting one of mammalian blood coagulation factors VII, VIII, IX, X, XI and XII, said process comprising adding to a mammalian fluid selected from the group consisting of blood and blood plasma a solution of sulfur dioxide present in an anticoagulantly effective amount.

2. The process of claim 1 in which said solution contains from about 1 to about 7 percent by weight of sulfur dioxide.

3. A process for lengthening both prothrombin time (PT) and partial thromboplastin time (PTT) in a mammalian fluid selected from the group consisting of blood and blood plasma, said process comprising treating said fluid with an aqueous solution of sulfur dioxide present in an anticoagulantly effective amount.

4. The process of claim 3 in which said solution contains from about 1 to about 7 percent by weight of sulfur dioxide.

5. A method of prolonging both the prothrombin time (PT) and partial thromboplastin time (PTT) of the blood or blood plasma of a mammal in need of such therapy, said method comprising orally administering to said mammal an anticoagulantly effective amount of an aqueous solution of sulfur dioxide and continuing said oral administration until the prothrombin time (PT) and thromboplastin time (PTT) are both prolonged as compared with PT and PTT values of the mammal's blood or blood plasma mesured prior to initiating said therapy.

6. The process of claim 3 in which said solution is orally administered to a human at a total dose of from about 1 to about 50 mg/kg of body weight/day.

* * * * *